United States Patent [19]

Robertson, Jr. et al.

[11] 4,267,845

[45] May 19, 1981

[54] METHOD AND APPARATUS FOR MEASURING PULMONARY VENTILATION

[76] Inventors: Charles H. Robertson, Jr., 4200 Oxford Circle East, Richmond, Va. 23221; Mark E. Bradley, 32 Orchard Way South, Rockville, Md. 20854

[21] Appl. No.: 948,789

[22] Filed: Oct. 5, 1978

[51] Int. Cl.³ .............................................. A61B 5/08
[52] U.S. Cl. .................................. 128/721; 128/725
[58] Field of Search ...................... 128/716, 720-723, 128/725

[56] References Cited

U.S. PATENT DOCUMENTS 3,483,861 12/1969 Tiep ................................. 128/721
3,911,899 10/1975 Hattes ........................... 128/721 X

FOREIGN PATENT DOCUMENTS 1563125 4/1969 France ................................ 128/716

OTHER PUBLICATIONS

Rolfe, "A Magnetometer . . . Infants", Proceedings 1st Convention in Bioengineering, Milan, Italy, Jun. 1972, pp. 1-7.
Hamilton et al., "Ventilation Monitor . . . Impedance Changes", Med. Res. Eng., vol. 11, No. 3, May-Jun. 1972, pp. 20-24.

Primary Examiner—Lee S. Cohen
Attorney, Agent, or Firm—James J. Brown

[57] ABSTRACT

A device and method are described for precisely measuring pulmonary ventilation without the need for mouthpiece, face masks or other inhibiting devices subsequent to calibration. Anterior-posterior and lateral displacement of both the rib cage and abdomen are measured during breathing by at least 4 sets of magnetometers. The signals from the magnetometers are fed along with an initial signal from a breath volume measuring device to a microprocessor which correlates these signals by a least squares analysis to give constants defining the relationship between the magnetometer signals and readouts of total ventilation; respiratory rate, tidal volume and relative proportion of rib cage versus abdomen volume. Once the device is calibrated, these parameters can readily be determined independently of any direct measurement of breath volume. It has been found particularly important that calibration be performed during rebreathing at volumes of 1-2 liters of air, breathed 3-6 times to reduce the noise to signal ratio.

3 Claims, 10 Drawing Figures

METHOD AND APPARATUS FOR MEASURING PULMONARY VENTILATION

STATEMENT OF THE INVENTION

The present invention is concerned with a device and precise method for determining pulmonary ventilation using multiple sets of magnetometers to measure anterior-posterior and lateral displacement of the rib cage and abdomen during breathing. More specifically, the present invention involves the use of at least four magnetometers to measure anterior-posterior and lateral displacement along with a microprocessor, readout and alarms to record the signal from the magnetometer.

BACKGROUND OF THE INVENTION

The monitoring of ventilation and its pattern has heretofore been difficult if not impossible in many situations where measurements are important. All previously employed means for accurately measuring ventilation have, for example, required the use of either a mouthpiece or a mask. Such masks or mouthpieces cannot always be used with critically ill patients. Further, these devices add dead space and resistance to the breathing which is being measured. Additionally, spirometers and flowmeters, which have frequently been heretofore used, limit the freedom of movement of individuals and their accuracy is adversly affected by changing environment.

In an attempt to overcome some of these difficulties, pairs of electromagnets and magnetometers have been placed on the surface of the rib cage and abdomen to measure linear dimension changes and estimate lung volume changes. However, single anterior-posterior pairs of magnetometers on the rib cage and abdomen, while fairly quantitative for quiet breathing become increasingly inaccurate as breath volume increases. This is also true during resistive breathing or forced expirations or when posture varies. As volume is increased from normal or during increased respiratory efforts, the rib cage and abdomen no longer behave with a single degree of freedom, so single magnetometer pairs cannot quantitatively measure these maneuvers. That is, there are changes in the cross-sectional dimensions of the chest wall in the lateral dimension which are not reflected in anterior-postierior movements.

It is, accordingly, an object of the present invention to provide an improved method and apparatus for the non-invasive, accurate measurement of ventilation, including pattern and fractionation.

It is a further object of the present invention to provide a system which dispenses with a mouthpiece or mask during measurement of ventilation and which can be used accurately in most environments and situations without constraining or requiring alteration of posture of the subject.

Still a further object of the present invention is to avoid a system which adds dead space and resistance to breathing while measurements are being made.

SUMMARY OF THE INVENTION

The above objectives are achieved according to the present invention by providing a system in which four pairs of magnetometers are placed in anterior-posterior and lateral positions across the rib cage and abdomen to measure all degrees of movement of the chest wall (rib cage and abdomen) during respiration. Signals produced by the magnetometers are converted by means of a microprocessor to produce multiple readouts of total ventilation, respiratory rate, tidal volume and relative percent respiration by rib cage versus abdomen.

Electromagnet and magnetometer pairs are attached to the chest of the subject with adhesive discs in the midline both anterior-posterior and laterally at the level of the nipples to measure rib cage movements and at the level 2–3 cm above the umbilicus to measure abdomen-diaphragm movements. It is important that the electromagnet and sensor in each pair were placed parallel to each other because if the angular relationship changes with respiration, errors in distance measurement will occur as the magnetic flux at the sensor will change.

Magnetometer outputs are zero surpressed to give no voltage signal at end expiration during quiet breathing.

In order to calibrate the system of the present invention 3-breaths are taken by the subject into a volume measuring device, the volume of each breath being about $1\frac{1}{2}$ liters. The volume and magnetometer voltage signals produced during the maneuver are low pass filtered with an active quadripole filter and analog to digital conversion performed using a microprocessor. The microprocessor performs a least squares analysis to determine the value of constants which produce the best fit of the volume and magnetometer data to mathematical models. These constants are used to determine lung volume changes from the magnetometer signals alone under all conditions thereafter.

Accordingly all that is then required is for the subject having the electromagnet-magnetometer pairs attached to be monitored in any desired condition.

The invention will, however, be more fully understood by having reference to the drawing, examples and further description which follows:

DETAILED DESCRIPTION OF THE INVENTION

Figure 1:
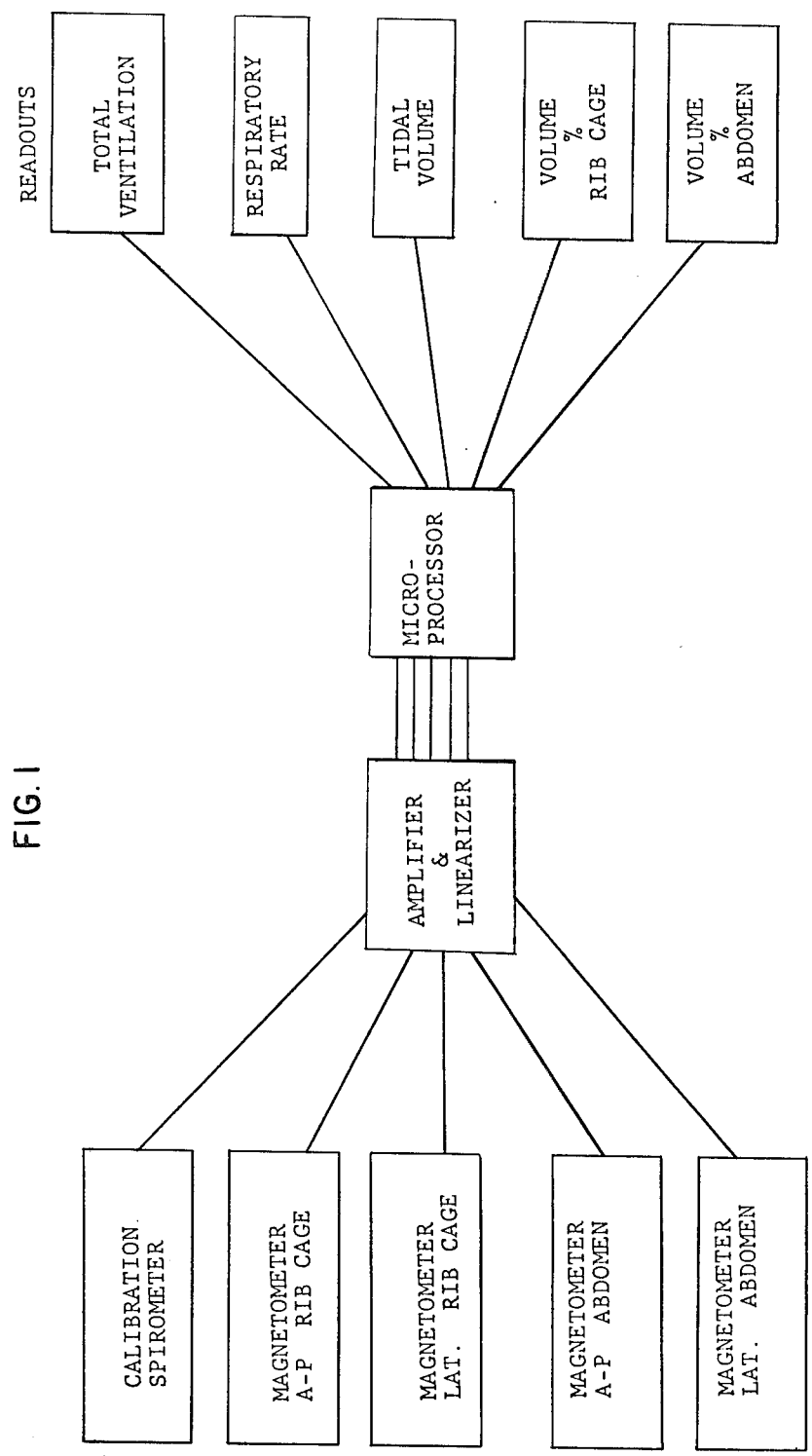
FIG. 1 is a schematic drawing of the system of the present invention.

Having reference to FIG. 1, which is a schematic representation of the present invention, four sets of magnetometer-electromagnet pairs are shown connected to a standard filtering and amplification system through which the discrete signals from each magnetometer pair passes. In addition, a calibration breath volume measuring device such as a spirometer or body plethysmograph is connected to the filtering and amplification system. The discrete signals from the filtering and amplification system pass to a micro-processor such as an LS1-11 (Digital Equipment Co., Maynard, Mass.) which perform an analog to digital conversion of the respective signals.

To calibrate the device, the micro-processor performs a least squares analysis on a mathematic model to determine constants which determine the best fit of the volume data from the volume measuring device and the magnetometer data. The constants so generated are used thereafter in conjunction with the magnetometer signals to determine lung volume change under all conditions with the magnetometer signals and appropriate mathematical model to determine lung volume change.

Upon completion of these steps, conversion of calculated parameters is performed, and these five signals are transmitted to digital or oscillographic readouts.

An integral part of the system of the present invention involves the use of mathematical models. During respiration the change in volume of the rib cage cylinder which contains the lungs can be approximated by the equation:

$$V = K_1 A_{RC} - K_2 (A_{RC}/A_{AB}) - K_3 \quad (1)$$

Where V is the volume of a breath, $K_1$, $K_2$ and $K_3$ are constants, $A_{RC}$ is area of the rib cage, $A_{AB}$ is area of the abdomen.

Since the change in lung volume that occurs with respiration is due partially to increasing rib cage dimension and partially to descent of the diaphragm and thus increases in abdominal diameter, the computer is programmed so that given the constants in the previous equation it could calculate the change in volume due to rib cage expansion ($\Delta V_{RC}$) as $$\Delta V_{RC} = \int [(K_1 - K_2)/A_{AB}] \delta A_{RC} \quad (2)$$

On the basis of this system readouts are obtained for ventilation Per Minute, Respiratory Rate, Tidal Volume, Fraction of Volume Change Attributed to Rib Cage versus Abdomen.

To verify results obtained according to the present invention, six subjects were tested. Table 1 describes the physical characteristics of these subjects. One subject was a smoker. None had overt pulmonary functional abnormalities. In an attempt to determine the applicability of the model to different body habitus, subjects were selected whose height/weight relationships varied considerably and whose resting chest wall dimensions were quite different. Electromagnet-magnetometer pairs were attached in accordance with the previously described procedures of the invention. The subjects were first seated in a volume plethysmograph breathing to the outside.

Figure 2:
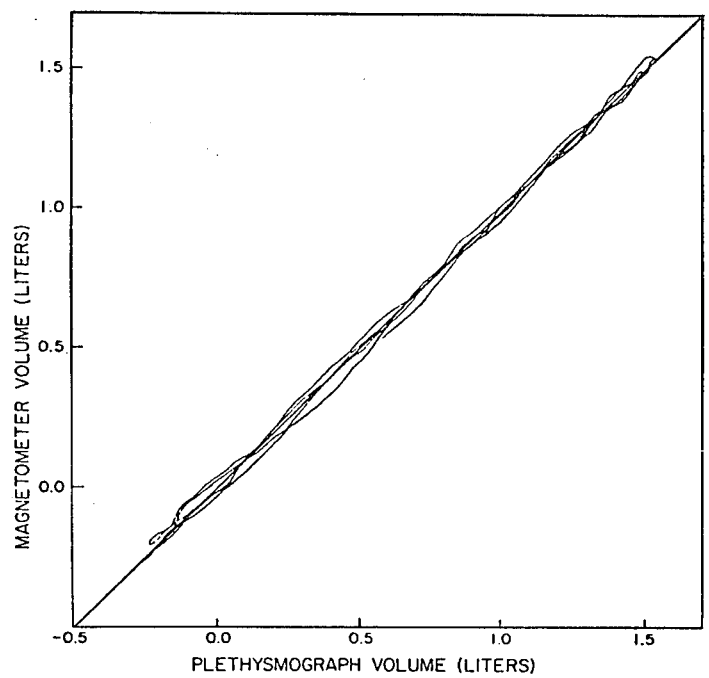
FIG. 2 shows a plot of the volume change measured by the magnetometers against the plethysmographic volume change during rebreathing in one of the subjects and is representative of the close correlation between the actual and estimated volume changes attained during calibration with the model.

Calibration was performed on breaths of approximately 1.5 liters produced by rebreathing in order to increase the signal-to-noise ratio. Equation (1) and least square analysis were used by the micro-processor to determine values of the constants which produced correlations between actual volume change and that calculated from the magnetometer signals. An example of the close correlation is shown in FIG. 2. Table 2 gives the numeric results in all of the subjects. Although there was a very high correlation between estimates of parameters (almost always 0.99 or higher), the percentage variation in parameter estimates (an index of the computer's ability to specify a parameter exactly) was low (highly specific), usually less than 2% of the parameter estimate.

Figure 3A:
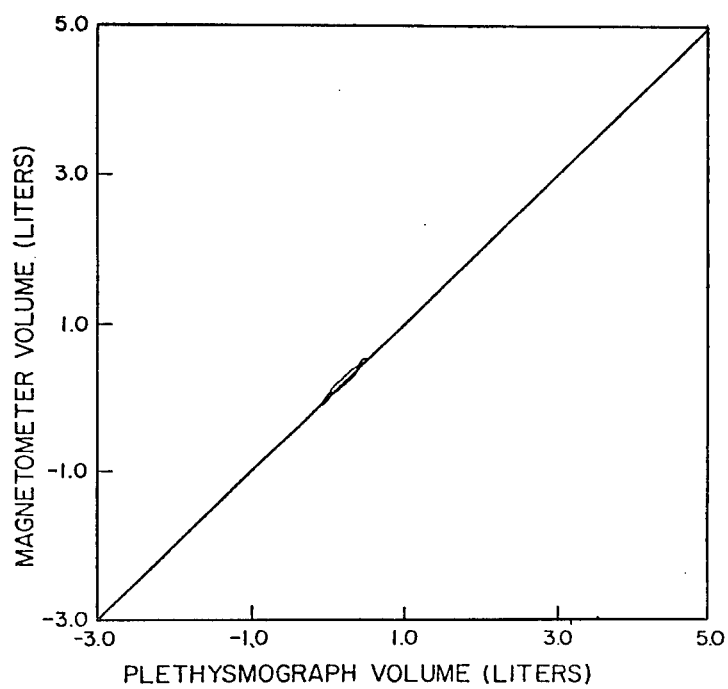
FIG. 3A demonstrates for a quiet breath the correlation obtained in a representative subject between plethysmographic volume change and volume change predicted by the magnetometers using the calibration parameters determined during larger tidal volumes induced by rebreathing.
Figure 3B:
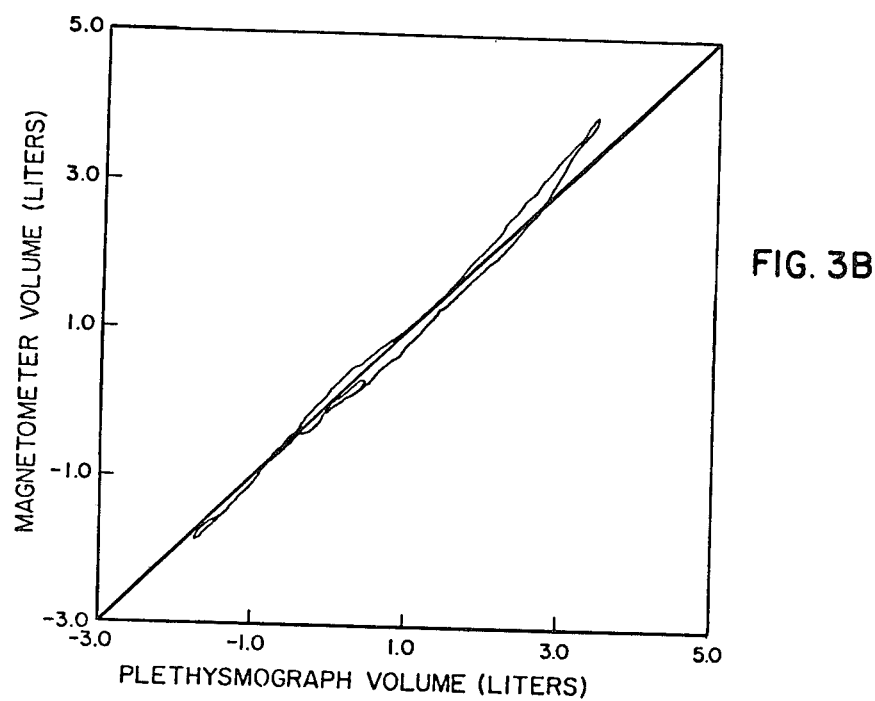
FIG. 3B demonstrates a vital capacity maneuver in the same subject and illustrates that a good correlation also results at volumes larger than those used for calibration.

Although a reasonable model was provided at rebreathing tidal volumes around 1.5 liters, it might be inapplicable to resting tidal volumes or very large tidal volumes which approach vital capacity. In order to assess this possibility the parameters determined during the calibration runs in each subject were used and their estimate of thoracic gas volume change compared with the plethysmographic value during quiet breathing and a vital capacity. Representative tracings for quiet breathing and a vital capacity in one subject are shown in FIG. 3A and 3B respectively. The correlation coefficients and variances for all subjects are given in Table 3.

For quiet breathing the parameters generated during rebreathing had excellent predictive value in all subjects with R values 0.95 or higher and variances of 2.5 milliliters or less (0.2 to 0.5% of the tidal volume being measured). Over the full range of the vital capacity the close correlation persisted, with R values 0.97 or higher. Variances around the line of identity were higher (14–121 milliliters) but still only an average of 1.2% of the volume measured.

Since the model assumes that the lungs exist inside a structure whose volume can be changed either in cross-sectional area (which itself has two degrees of freedom, A-P and lateral) or in height, the computer program contained the capacity to calculate the volume contributed by height change, $\int A dh$, and that contributed by cross-sectional area change, $\int h dA$. These differentials correspond to the volume moved by the diaphragm-abdominal muscles and rib cage muscles respectively. (Equation 2)

Figure 4A:
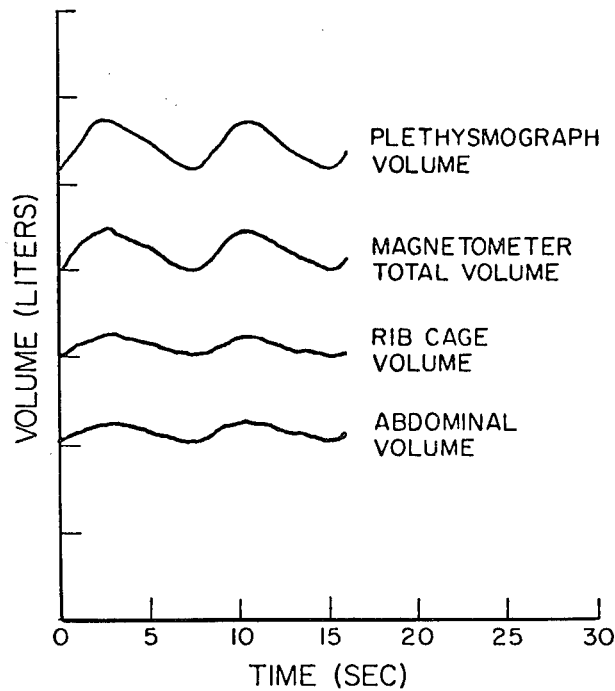
FIG. 4 shows examples of the fractionation of ventilation between rib cage and abdomen-diaphragm volume changes for quiet breathing (A) and a vital capactity (B).
Figure 4B:
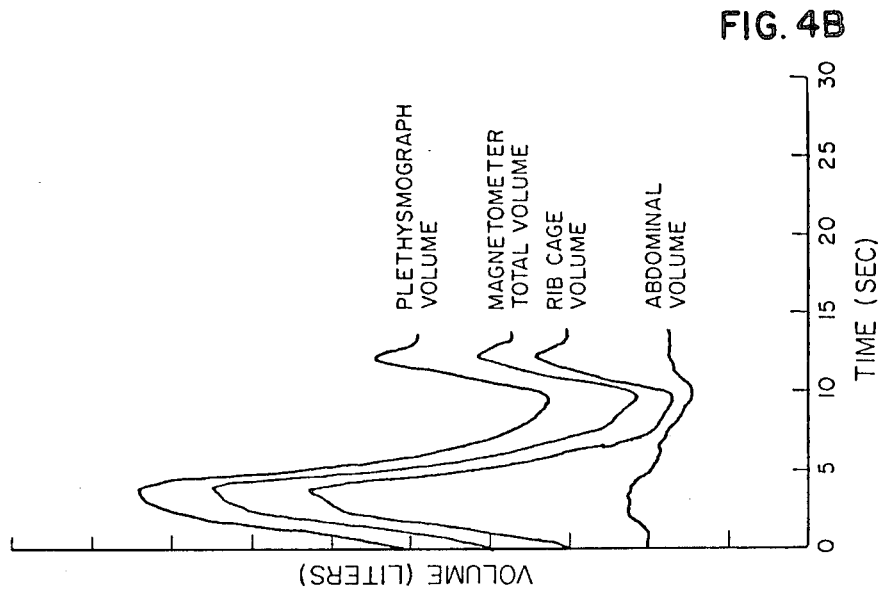

FIG. 4A shows an example of the fractionation of volume moved by the rib cage and abdomen-diaphram during quiet breathing in one of the subjects. The finding in these subjects sitting upright that 74% (range 47–91%) of the volume change was accomplished by the rib cage and 26% by the abdomen-diaphragm is similar to previous estimates of the fractionation by other techniques.

To assess the utility of the method for measuring lung volume changes during more strenuous respiratory efforts than unloaded quiet breathing, slow vital capacities or rebreathing, two subjects performed forced vital capacity maneuvers and breathed against external expiratory and inspiratory resistances while seated in the plethysmograph. This comparison is particularly crucial in light of the recent observations demonstrating that there are changes in the configuration of the chest wall during forced expiration which make only A-P dimension changes incapable of measuring the volume change accurately. Thus, the forced vital capacity and other large respiratory efforts represent a test of whether the four channel magnetometer model offers the benefit of being usable under conditions where a similarly computerized two channel system would falter.

Figure 5A:
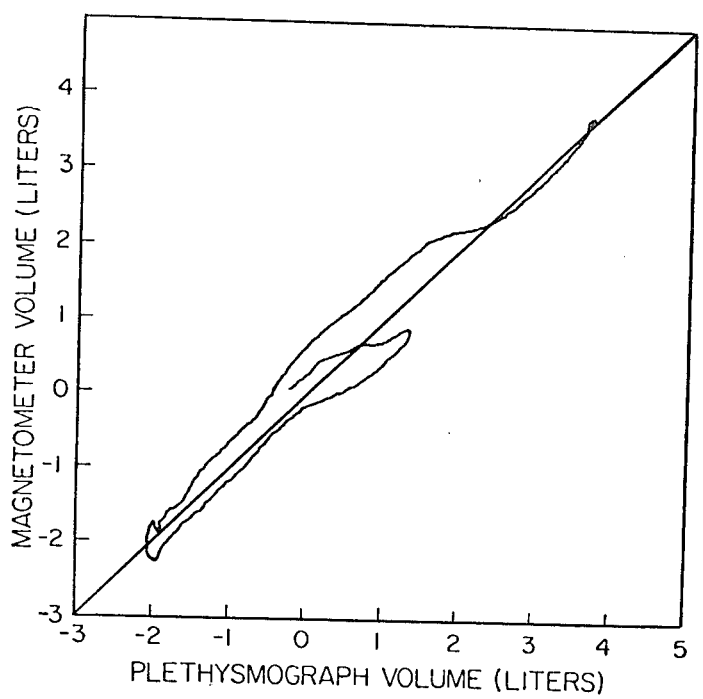
FIG. 5A gives the correlation of magnetometer and plethysmographic volume changes during a forced expiratory vital capacity and the subsequent inspiration.

Using the calibration parameters generated during rebreathing, there was good correlation between plethysmographic volume change and the volume predicted by the four channel magnetometers during the forced vital capacity maneuver (R −0.99 and 0.98 with variances of 68 and 100 ml in the two subjects). An example of the correlation is shown in FIG. 5A. The expiratory and inspiratory resistances were also well predicted (R=0.99 and 0.98 with variances of 1.7 and 12.3 ml for expiratory resistance, and R=0.98 and 0.93 with variances of 3.7 and 29.7 ml for inspiratory resistance).

Figure 5B:
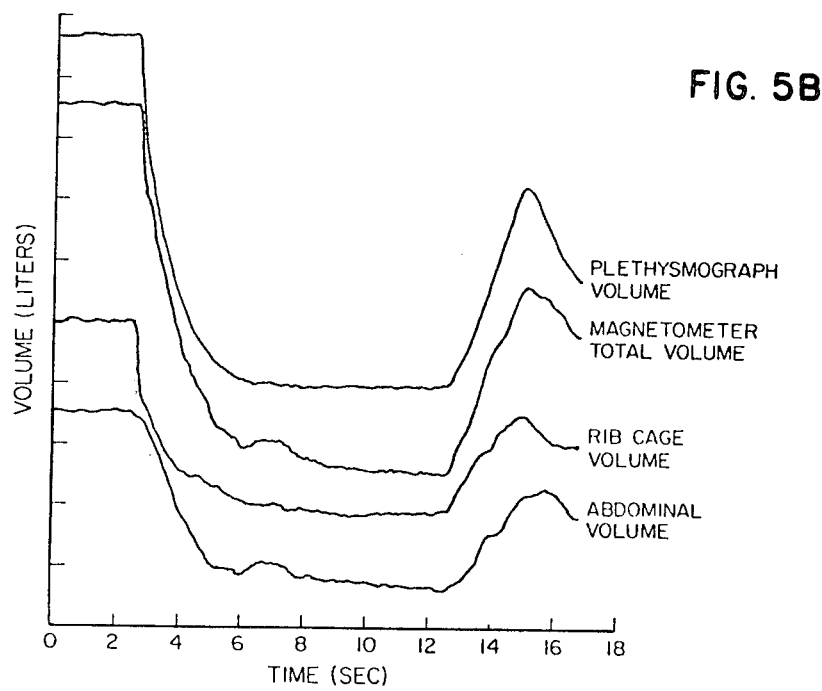
FIG. 5B plots plethysmographic volume change, total magnetometer volume and volume changes for the rib cage and abdomen during the same forced expiratory vital capacity as 5A illustrate the similar abdomen-rib cage fractionation as in the slow vital capacities.

The fractionation of the forced vital capacity between rib cage and abdomen is illustrated in FIG. 5B. The relative amount contributed by the abdomen or rib cage was essentially the same as that observed for the slow vital capacity maneuvers in these two subjects.

If the method of determining ventilatory volume and fractionating it between rib cage and diaphragm-abdomen is to have a major role in physiologic monitoring, it must be relatively unaffected by posture or movement. In order to assess whether this technique was sufficiently accurate under those various conditions to be usable, a series of measurements were performed on one subject who was outside the box but breathing into it through a flexible tube. This allowed movement and changes in posture. Calibration of the magnetometers was performed with the subject rebreathing from the plethysmograph standing erect and motionless. The parameters so generated were used to predict ventilatory volume while rocking from side to side erect, walking in-situ, sitting, lying supine, and lying in the left lateral decubitus position.

Figure 6A:
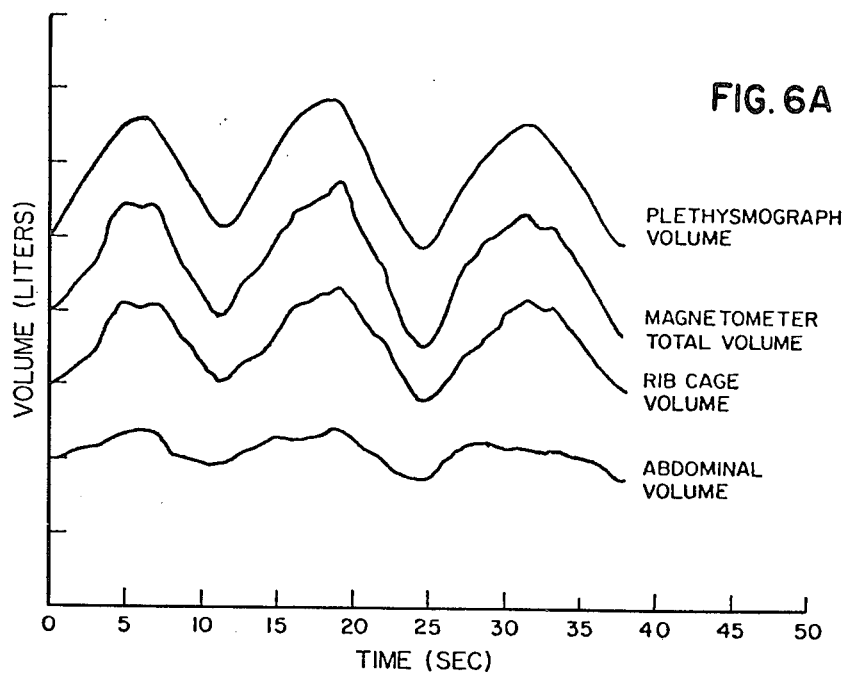
FIG. 6 shows the capacity of the magnetometers to measure ventilation despite movements and position changes which are illustrated by these tracings of volumes vs time (A) and magnetometer volume vs plethysmographic volume (B) during walking.
Figure 6B:
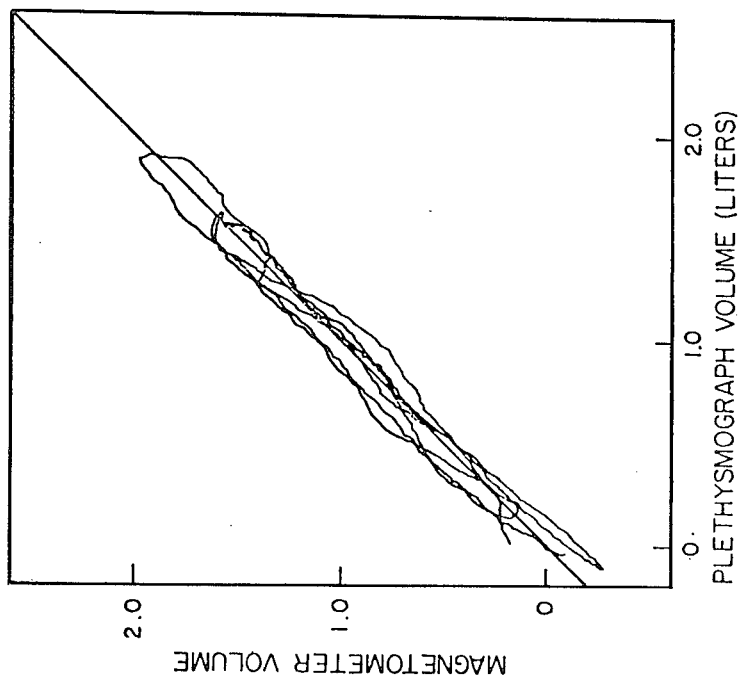

During rocking, the model predicted volume quite accurately (R=0.98, variance 4.1 m.). During walking (FIG. 6) the R value remained fairly good (0.97), but the variance rose to 17.7 ml. The step artifacts can readily be observed in the tracings and could be corrected for by extrapolation or averaging techniques if the magnetometers were to be used for exercise monitoring. The high correlation persisted for the sitting (R=0.98, variance 9.1 ml) and lying supine positions (R=0.99, variance 0.9 ml), but decreased slightly in the decubitus position (R=0.95, variance 15.9 ml).

TABLE 1

| PHYSICAL CHARACTERISTICS OF SUBJECTS | | | | | | | | |
|---|---|---|---|---|---|---|---|---|
| | | | | BODY | RIB CAGE | | ABDOMEN | |
| SUBJECT | AGE | HEIGHT | WEIGHT | HABITUS | $D_{AP}$ | $D_{LAT}$ | $D_{AP}$ | $D_{LAT}$ |
| 1 | 31 | 180 cm | 70 kg | ecto | 20.4 cm | 33.2 cm | 18.1 cm | 29.2 cm |
| 2 | 25 | 185 cm | 84 kg | meso | 20.7 cm | 36.0 cm | 20.7 cm | 30.5 cm |
| 3 | 24 | 178 cm | 86 kg | endo | 23.8 cm | 35.8 cm | 26.8 cm | 33.3 cm |
| 4 | 25 | 183 cm | 68 kg | ecto | 16.6 cm | 26.8 cm | 17.3 cm | 26.3 cm |
| 5 | 28 | 178 cm | 84 kg | meso | 21.3 cm | 36.2 cm | 26.4 cm | 32.9 cm |
| 6 | 54 | 185 cm | 97 kg | endo | 29.6 cm | 40.4 cm | 29.5 cm | 35.2 cm |

TABLE 2

| FIT OF INITIAL CALIBRATION | | | | |
|---|---|---|---|---|
| Subject | R Value | Variance | $K_1$ | Chest Wall Height* |
| 1 | .997 | 2.17 ml | 48 cm | 48 cm |
| 2 | .999 | .64 ml | 55 cm | 57 cm |
| 3 | .995 | 1.39 ml | 55 cm | 56 cm |
| 4 | .994 | 2.14 ml | 63 cm | 55 cm |
| 5 | .996 | 1.59 ml | 54 cm | 56 cm |
| 6 | .999 | 1.44 ml | 57 cm | 59 cm |
| Mean | .997 | 1.56 ml | 55 cm | 55 cm |

*Height from sternal notch to symphysis pubis.

TABLE 3

| PREDICTIVE CAPACITY OF MODEL | | | | |
|---|---|---|---|---|
| | Quiet Breathing | | Vital Capacity | |
| Subject | R Value | Variance | R Value | Variance |
| 1 | .99 | .9 ml | .98 | 45 ml |
| 2 | .96 | 2.4 ml | .98 | 121 ml |
| 3 | .98 | 1.4 ml | .97 | 89 ml |
| 4 | .99 | 1.1 ml | .99 | 14 ml |
| 5 | .95 | 2.5 ml | .99 | 36 ml |
| 6 | .99 | 1.7 ml | .98 | 58 ml |
| Mean | .98 | 1.7 ml | .98 | 61 ml |

We claim:

1. A device for measuring pulmonary ventilation comprising microprocessor means for receiving discrete electrical signals and at least 4 sets of magnetometer means for measuring lateral and anterior displacement of the rib cage and abdomen during breathing and calibration means for measuring the volume of breaths taken during breathing; said magnetometer means and calibration means generating discrete analog electrical signals in response to said measured displacement and volume respectively and being connected to said microprocessor means for receiving said discrete electrical signals from each of said magnetometer means and said calibration means and performing an analog to digital conversion on said signals; a plurality of readout means being connected to said microprocessor means for receiving said digital signals and displaying separate readouts for total pulmonary ventilation, respiratory rate, tidal volume, and comparative volume contributed by rib cage and abdomen.

2. A method for measuring pulmonary ventilation which comprises, attaching at least 4 sets of magnetometer means for measuring displacement of the rib cage and abdomen during breathing as follows:

one set each in the anterior-posterior and lateral positions relative to the rib cage and, one set each in the anterior-posterior and lateral positions relative to the abdomen;

generating a discrete analog electrical signal from each of said magnetometer means, said signal corresponding to linear displacement during breathing; initially, simultaneously measuring the volume of each breath with a volume measuring means and generating a corresponding additional discrete electrical signal proportional thereto; feeding said discrete electrical signals to a microprocessor for performing an analog to digital conversion on said signals and feeding the digital signals to readout means for displaying parameters corresponding to total pulmonary ventilation, respiratory rate, tidal volume and comparative volume contributed by rib cage and abdomen; and microprocessor receiving said discrete electrical signals initially performing a calibration by carrying out a least squares analysis of said signals to determine constants defining the relationship of volume of air breathed with the signals from said magnetometer means, and subsequently determining said displayed parameters from further magnetometer means signals independently of measurements of air volume.

3. The method of claim 2 wherein said initial measurement of the volume of each breath and calibration are carried out with the subject taking 3-6 breaths into said volume measuring means, each of said breaths having a volume of about 1-2 liters.

* * * * *